United States Patent
Sano et al.

(10) Patent No.: US 11,154,270 B2
(45) Date of Patent: Oct. 26, 2021

(54) X-RAY IMAGING APPARATUS

(71) Applicant: Shimadzu Corporation, Kyoto (JP)

(72) Inventors: Satoshi Sano, Kyoto (JP); Kenji Kimura, Kyoto (JP); Taro Shirai, Kyoto (JP); Takahiro Doki, Kyoto (JP); Akira Horiba, Kyoto (JP); Naoki Morimoto, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 16/958,044

(22) PCT Filed: Nov. 6, 2018

(86) PCT No.: PCT/JP2018/041152
§ 371 (c)(1),
(2) Date: Jun. 25, 2020

(87) PCT Pub. No.: WO2019/142451
PCT Pub. Date: Jul. 25, 2019

(65) Prior Publication Data
US 2021/0059630 A1 Mar. 4, 2021

(30) Foreign Application Priority Data
Jan. 19, 2018 (JP) .............................. JP2018-007624

(51) Int. Cl.
*G01N 23/046* (2018.01)
*G01N 23/201* (2018.01)
*A61B 6/00* (2006.01)

(52) U.S. Cl.
CPC .......... *A61B 6/5282* (2013.01); *A61B 6/4035* (2013.01); *A61B 6/4291* (2013.01); *A61B 6/466* (2013.01); *A61B 6/5205* (2013.01)

(58) Field of Classification Search
CPC ............... G01N 23/046; G01N 23/201; G01N 2223/419; G01N 2223/045; G01N 23/20025; A61B 6/5282; A61B 6/4035; A61B 6/466; A61B 6/5205; A61B 6/4291
See application file for complete search history.

(56) References Cited

U.S. PATENT DOCUMENTS

2019/0331616 A1* 10/2019 Schaff .............. G01N 23/20025

OTHER PUBLICATIONS

Bech et al., "Quantitative X-ray dark-field computed tomography" Physics in Medicine and Biology 55 (2010) p. 5529-p. 5539.
Written Opinion by the International Search Authority dated May 2, 2019 for PCT application PCT/JP2018/041152, submitted with a machine translation.

* cited by examiner

*Primary Examiner* — Don K Wong
(74) *Attorney, Agent, or Firm* — Muir Patent Law, PLLC

(57) ABSTRACT

This X-ray imaging apparatus (100) includes a rotation mechanism (8) for relatively rotating an imaging system (200) constituted by an X-ray source (1), a detector (5), a first grating (2) and a second grating (3), and an image processing unit (6) for generating a dark-field image based on an X-ray intensity distribution at each of a plurality of rotation angles. The image processing unit (6) is configured to perform a scattering correction for reducing a dark-field signal of a pixel whose dark-field signal is larger than a threshold value (V1) among a plurality of pieces of pixels in the dark-field image to a set value (V2).

8 Claims, 12 Drawing Sheets

(a) Fiber bundle is arranged in a direction perpendicular to the light axis of the X-rays (b) Cross-sectional view taken along the line 400-400

(c) Fiber bundle is arranged so as to be inclined with respect to the light axis of the X-rays (d) Cross-sectional view taken along the line 500-500

With scattering correction

X-RAY IMAGING APPARATUS

TECHNICAL FIELD

The present invention relates to an X-ray imaging apparatus, and more specifically to an X-ray imaging apparatus equipped with an image processing unit for generating a dark-field image of a subject.

BACKGROUND OF THE INVENTION

Conventionally, an X-ray imaging apparatus equipped with an image processing unit for generating a dark-field image of a subject is known. Such an X-ray imaging apparatus is disclosed, for example, in M Bech, et al. "Quantitative X-ray dark-field computed tomography" PHYSICS IN MEDICINE AND BIOLOGY 55 (2010) p. 5529-p. 5539.

The X-ray imaging apparatus of the aforementioned "quantitative X-ray dark-field computed tomography" PHYSICS IN MEDICINE AND BIOLOGY 55 (2010) p. 5529-p. 5539 is provided with a phase grating, a detector, and an image processing device. The X-rays from the X-ray source are scattered by a subject, pass through the phase grating, and are emitted to a detector. Based on the interference intensity of the X-rays detected by the detector, a dark-field image is generated by the image processing device. An image is reconstructed using the dark-field image generated at each of the angles when the subject is rotated by 360 degrees.

In the conventional X-ray imaging apparatus as described in the aforementioned M Bech, et al. "Quantitative X-ray dark-field computed tomography" PHYSICS IN MEDICINE AND BIOLOGY 55 (2010) p. 5529-p. 5539, it can be approximated that in cases where the scattering of X-rays is sufficiently small, when the interference intensity of the X-rays is attenuated exponentially with respect to the transmission length of the scatterer. In this case, the reconfiguration can be appropriately performed by a common FBP (Filtered Back Projection).

PRIOR ART DOCUMENT

Non-Patent Document

Non-Patent Document 1: M Bech, et al., "Quantitative X-ray dark-field computed tomography" PHYSICS IN MEDICINE AND BIOLOGY 55 (2010) p. 5529-P. 5539

SUMMARY OF THE INVENTION

Problems to be Solved by the Invention

However, in the conventional X-ray imaging apparatus as described in the aforementioned M Bech, et al. "Quantitative X-ray dark-field computed tomography" PHYSICS IN MEDICINE AND BIOLOGY 55 (2010) P. 5529-P. 5539", when the scattering angle of the X-rays is large, the interference intensity of the X-rays does not change exponentially with respect to the transmission length, and therefore, the reconstruction by an FBP cannot be performed appropriately. That is, artifacts (noises) are generated in the dark-field image (three-dimensional data) reconstructed by the FBP. In this case, there is a disadvantage that the reconstructed image of the subject becomes blurred.

The present invention has been made to solve the above-mentioned problems, and an object of the present invention is to provide an X-ray imaging apparatus capable of suppressing blurring of a reconstructed image of a subject.

Means for Solving the Problem

In order to achieve the aforementioned object, an X-ray imaging apparatus according to one aspect of the present invention includes:

an X-ray source;

a detector configured to detect X-rays emitted from the X-ray source;

a plurality of gratings arranged between the X-ray source and the detector, the plurality of gratings including a first grating and a second grating;

a rotation mechanism configured to relatively rotate a subject and an imaging system composed of the X-ray source, the detector, and the plurality of gratings; and an image processing unit configured to generate a dark-field image due to scattering of the X-rays based on an X-ray intensity distribution detected by the detector at each of a plurality of rotation angles when rotated by the rotation mechanism, wherein the image processing unit is configured to perform a scattering correction for reducing a value based on X-ray scattering intensity of a pixel in which the value based on the X-ray scattering intensity is larger than a predetermined threshold value among a plurality of pixels in the dark-field image to a predetermined set value.

Note that the "dark-field image" refers to a visibility image obtained by a change in visibility based on small-angle scattering of an object. The dark-field image is also called a small-angle scattered image. The "visibility" refers to sharpness.

In the X-ray imaging apparatus according to one aspect of the present invention, as described above, it is configured such that the value based on the X-ray scattering intensity of a pixel in which the value based on the X-ray scattering intensity is larger than the predetermined threshold value is reduced to the predetermined set value. Thereby, even in cases where the value based on the X-ray scattering intensity does not change exponentially with respect to the transmission length (of the X-rays) that changes in response to the rotation angle prior to the scattering correction, the change of the value based on the X-ray scattering intensity with respect to the rotation angle (transmission length) can be approximated to the exponential change by reducing the value based on the X-ray scattering intensity to an appropriate value by optimizing the predetermined set value in the scattering correction. As a result, it is possible to suppress the generation of artifacts (noises) due to the large X-ray scattering angle and to suppress blurring of the reconstructed image of the subject.

In the X-ray imaging apparatus according to the aforementioned one aspect of the present invention, preferably, the image processing unit is configured to set, in the scattering correction, the value based on the X-ray scattering intensity of the pixel in which the value based on the X-ray scattering intensity is larger than the predetermined threshold value to the predetermined threshold value. With this configuration, it is possible to suppress an increase in the work load required for the user to determine the predetermined set value as compared with the case in which the predetermined set value and the predetermined threshold value are set to separate values.

In the X-ray imaging apparatus according to the aforementioned one aspect of the present invention, preferably, the subject includes a fiber bundle, the first grating includes a first grating structure part, the second grating includes a second grating structure part extending along a direction in which the first grating structure part extends, and the image processing unit is configured to perform the scattering correction on the dark-field image of the subject including the fiber bundle in cases where a direction in which a rotation axis of the rotation mechanism extends and a direction in which each of the first grating structure part and the second grating structure part extends are aligned.

Here, generally, in a dark-field image, a fiber bundle extending along the direction in which each of the first grating structure part and the second grating structure part extends appears remarkably. However, in cases where the direction in which the rotation axis of the rotation mechanism extends and the direction in which each of the first grating structure part and the second grating structure part extends are aligned, a fiber bundle that extends in a direction perpendicular to the direction in which each of the first grating structure part and the second grating structure part extends appears in addition to a fiber bundle that extends along the direction in which each of the first grating structure part and the second grating structure part extends. This is because, depending on the rotation angle, in some cases, the X-ray transmission length with respect to a fiber bundle extending in a direction perpendicular to the direction in which each of the first grating structure part and the second grating structure part extends is increased (in angle) by rotating the subject by the rotation mechanism. Therefore, the X-ray scattering angle by the fiber bundle extending in a direction perpendicular to the direction in which each of the first grating structure part and the second grating structure part extends becomes large. Therefore, in cases where a direction in which the rotation axis of the rotation mechanism extends and a direction in which each of the first grating structure part and the second grating structure part extends are aligned, by performing the scattering correction on the dark-field image of the subject including the fiber bundle, it is possible to more effectively suppress generation of artifacts (noises) due to scattering of X-rays by the fiber bundle extending in a direction perpendicular to the direction in which each of the first grating structure part and the second grating structure part extends. As a result, blurring of the reconstructed image of the subject can be more effectively suppressed.

In this case, preferably, the fiber bundle includes a first fiber bundle extending in a predetermined direction and a second fiber bundle extending in a direction other than the predetermined direction, and the image processing unit is configured to reduce a sum of a value based on X-ray scattering intensity due to the first fiber bundle and a value based on the X-ray scattering intensity due to the second fiber bundle to the predetermined set value by the scattering correction. With this configuration, unlike the case in which the value based on the X-ray scattering intensity due to the first fiber bundle and the value based on the X-ray scattering intensity due to the second fiber bundle are separately reduced by the scattering correction, the value based on the X-ray scattering intensity can be controlled by a single scattering correction. As a result, it is possible to suppress the time required for the scattering correction from becoming longer.

In the X-ray imaging apparatus for reducing the sum of the value based on the X-ray scattering intensity due to the first fiber bundle and the value based on the X-ray scattering intensity due to the second fiber bundle to a predetermined set value, preferably, one of the first fiber bundle and the second fiber bundle is provided so as to extend along a direction in which each of the first grating structure part and the second grating structure part extends, and the other of the first fiber bundle and the second fiber bundle is provided so as to extend along a direction perpendicular to a direction in which each of the first grating structure part and the second grating structure part extends when the first grating and the second grating are viewed from a front. According to this configuration, it is possible to suppress the generation of artifacts (noises) due to the X-ray scattering by one of the first fiber bundle and the second fiber bundle extending in a direction perpendicular to the direction in which each of the first grating structure part and the second grating structure part extends by the scattering correction. As a result, it is possible to suppress blurring of the image of the other of the first fiber bundle and the second fiber bundle extending along the directions in which each of the first grating structure part and the second grating structure part extends.

In the X-ray imaging apparatus in which the scattering correction is performed when the direction in which the rotation axis extends and the direction in which each of the first grating structure part and the second grating structure part extends are aligned, preferably, the image processing unit is configured to generate first three-dimensional dark-field data by performing the scattering correction on the dark-field image at each of the plurality of rotation angles and reconstructing the dark-field image at each of the plurality of rotation angles for which the scattering correction has been performed in cases where a direction in which a rotation axis of the rotation mechanism extends and a direction in which each of the first grating structure part and the second grating structure part extends are aligned. With this configuration, at each of the plurality of rotation angles, the dark field signal (a value based on the X-ray scattering intensity) can be made close to the change of the exponential attenuation, so that it is possible to suppress blurring of the first three-dimensional dark-field data.

In this case, preferably, the image processing unit is configured to accept a change whether or not the scattering correction is performed, and in cases where a direction in which the rotation axis extends and the direction in which each of the first grating structure part and the second grating structure part extends are substantially orthogonal when the first grating and the second grating are viewed from the front, second three-dimensional dark-field data is generated by reconstructing the dark-field image at each of the plurality of rotation angles without performing the scattering correction and a three-dimensional image of the subject is obtained by combining the first three-dimensional dark-field data and the second three-dimensional dark-field data. Here, generally, in a dark-field image, in cases where the direction in which the rotation axis extends and the direction in which each of the first grating structure part and the second grating structure part extends are substantially perpendicular to each other when the first grating and the second grating are viewed from the front, the fiber bundle extending along the direction in which each of the first grating structure part and the second grating structure part extends appears remarkably in the dark-field image. This is because, when the subject is rotated by the rotation mechanism, there is the dark-field sensitivity to the fiber bundle at any rotation angle with respect to the fiber bundle extending in the direction (the direction along the rotation axis) perpendicular to the direction in which each of the first grating structure part and the second grating structure part extends and the X-ray transmission length does not change greatly by the rotation angle. This results in fiber bundles in which a fiber bundle displayed prominently in the second three-dimensional dark-field data and a fiber bundle displayed prominently in the first three-dimensional dark-field data differ (extend in different directions) from each other. Therefore, by combining the first three-dimensional dark-field data and the second three-dimensional dark-field data, the user can visually recognize the positional relation between the fiber bundle which is remarkably displayed on the first three-dimensional dark-field data and the fiber bundle which is remarkably appeared on the second three-dimensional dark-field data on a three-dimensional image.

In the X-ray imaging apparatus according to the aforementioned one aspect of the present invention, preferably, the image processing unit is configured to accept a change of the predetermined set value. With this configuration, since the predetermined set value can be changed according to the type of the subject, the scattering correction can be performed more appropriately.

Effects of the Invention

According to the present invention, as described above, it is possible to suppress blurring of the reconstructed image of the subject.

Figure 2:
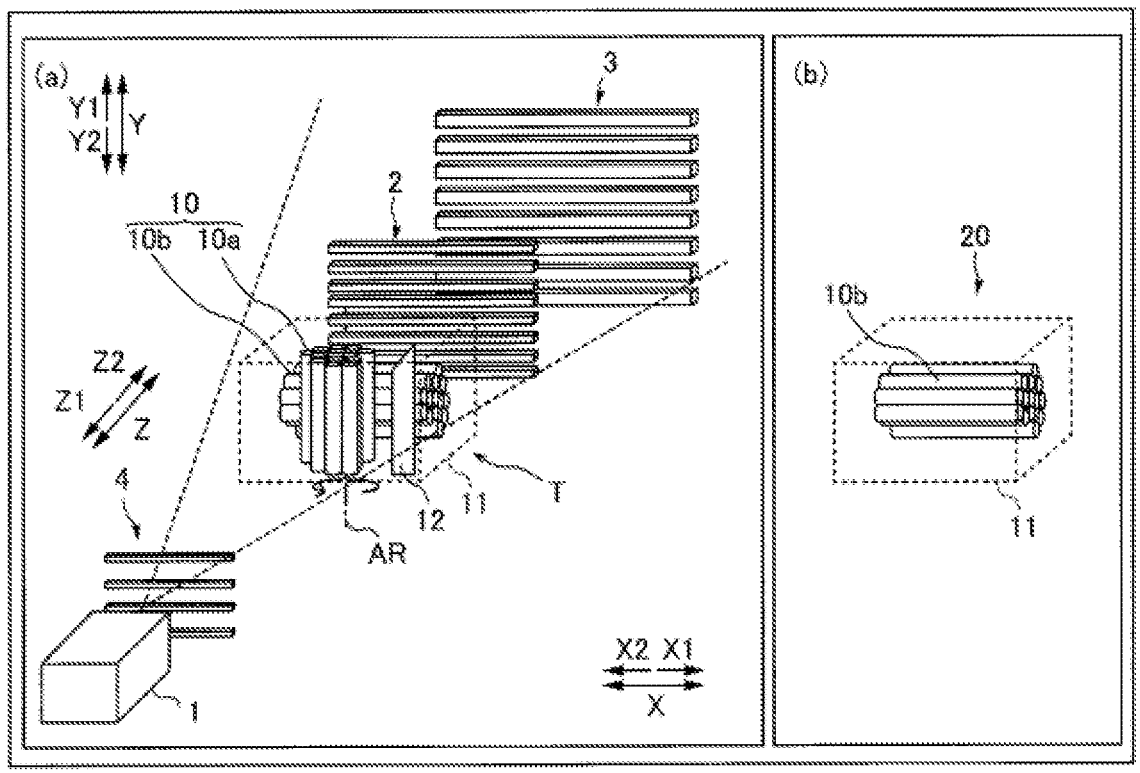

(a) of FIG. 2 is a configuration diagram showing a configuration of an X-ray imaging apparatus when a rotation axis and a grating direction are perpendicular to each other. (b) of FIG. 2 is three-dimensional dark-field data in the case of (a) of FIG. 2.

Figure 3:
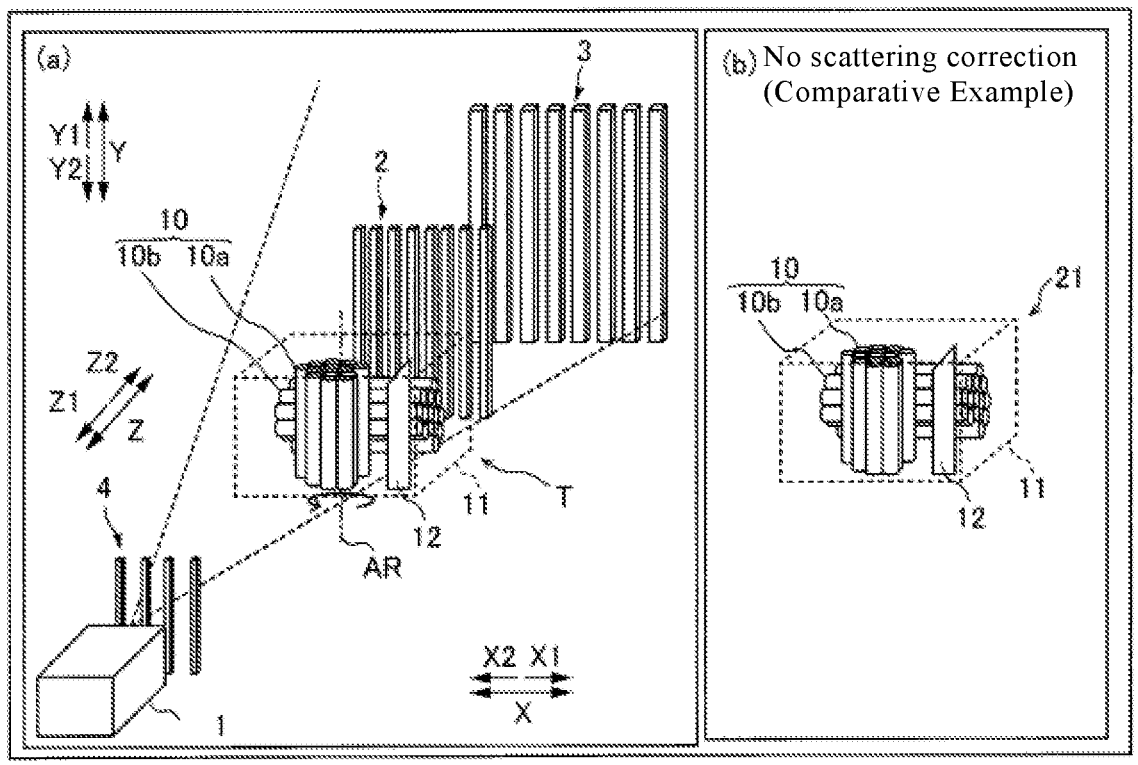

(a) of FIG. 3 is a configuration diagram showing the configuration of the X-ray imaging apparatus when the rotation axis and the grating direction are aligned. (b) of FIG. 3 is three-dimensional dark-field data (Comparative Example) of (a) of FIG. 3 (no scattering correction).

Figure 4:
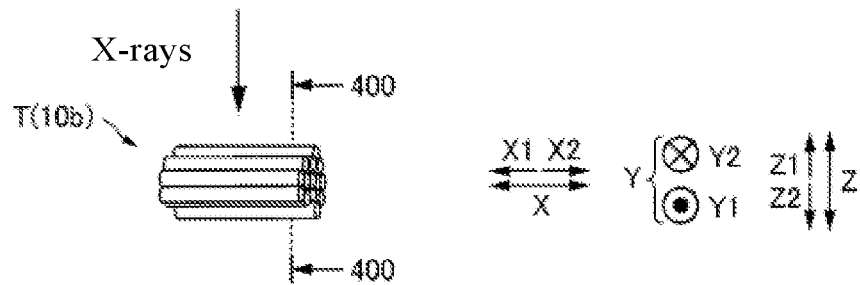
Figure 4:
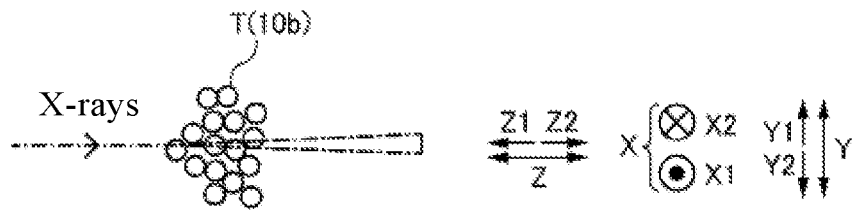
Figure 4:
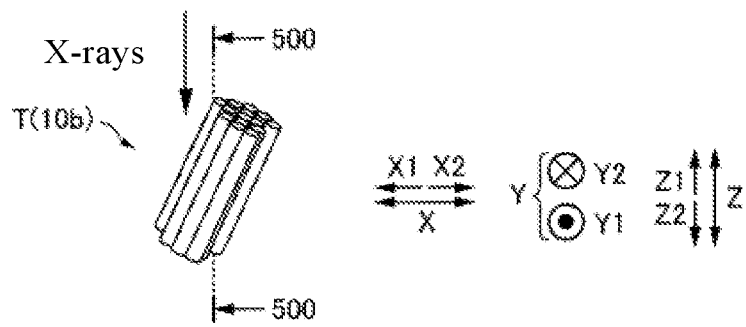
Figure 4:
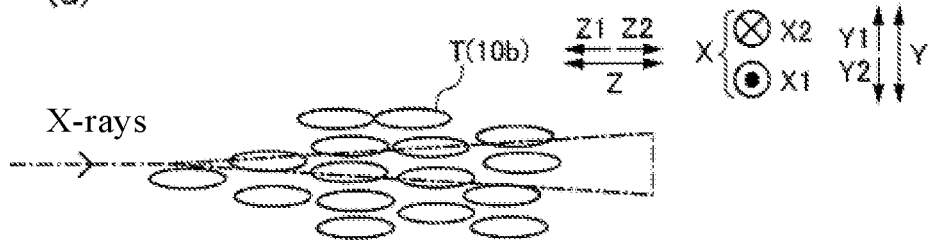

(a) to (d) of FIG. 4 are schematic diagrams for explaining arrangement angles of a subject with respect to an optical axis of X-rays and scattering degrees of the X-rays in the X-ray imaging apparatus according to one embodiment.

Figure 5:
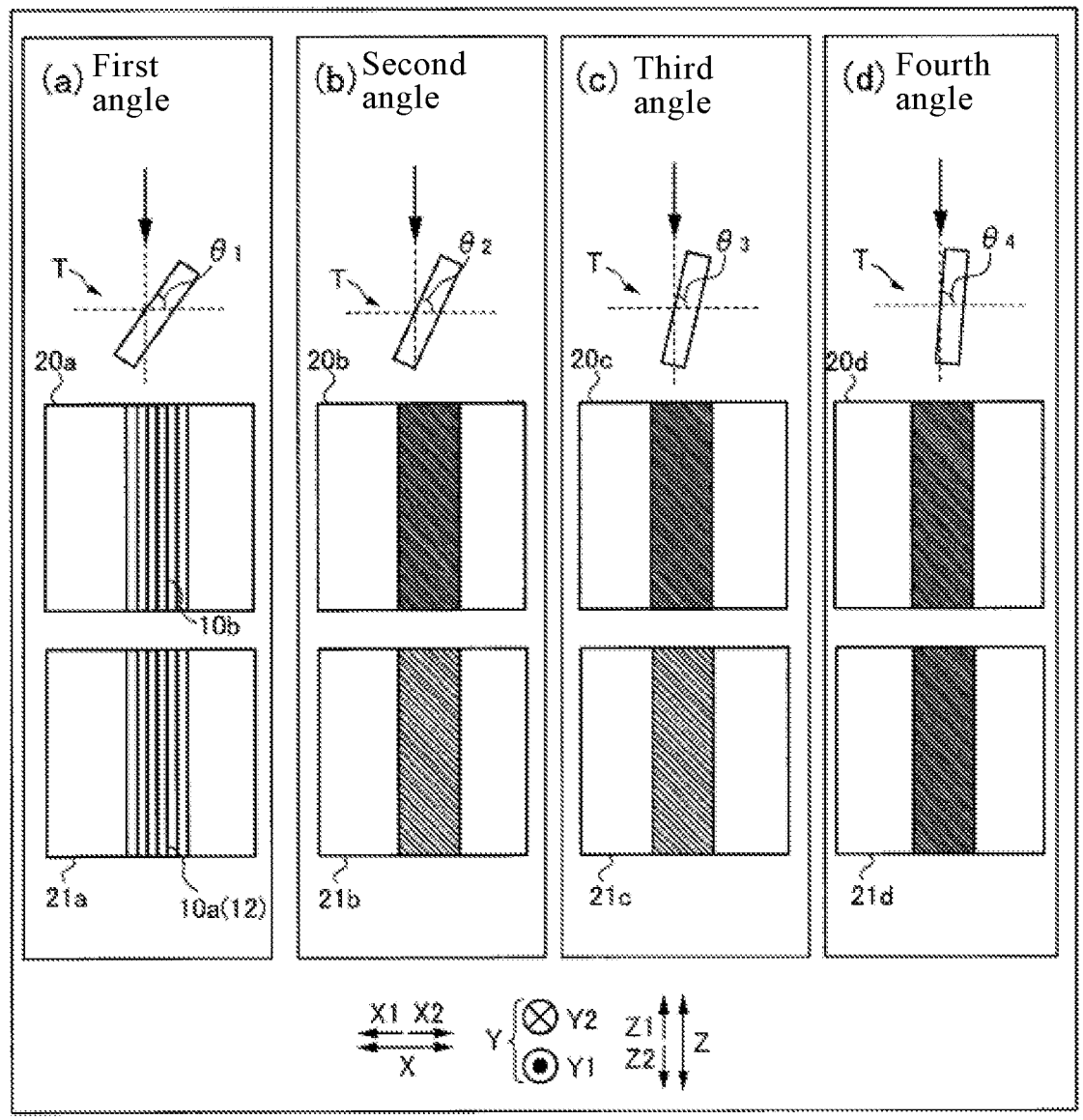

(a) to (d) of FIG. 5 are schematic diagrams of dark-field images when imaging is performed while rotating a subject with the X-ray imaging apparatus according to one embodiment.

Figure 6:
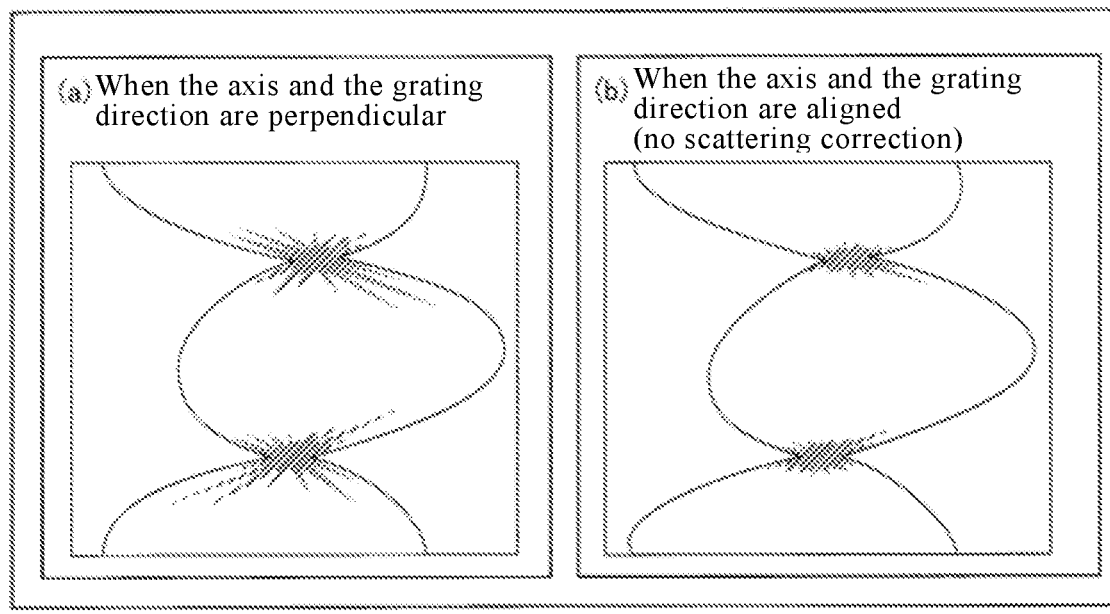

FIG. 6 is a sinogram of a dark-field image generated by the X-ray imaging apparatus according to one embodiment, wherein (a) of FIG. 6 is a diagram of the case of (a) of FIG. 2, and (b) of FIG. 6 is a diagram of the case of (a) of FIG. 3 (with no scattering correction).

Figure 7:
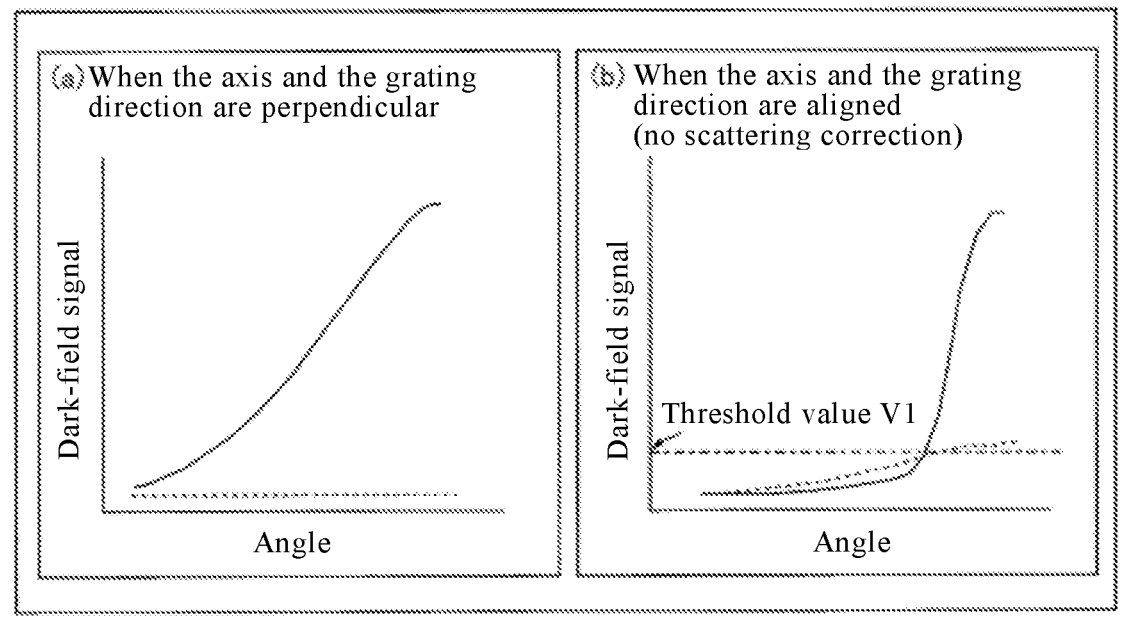

FIG. 7 is a diagram for explaining a relationship between a dark-field signal due to a first fiber bundle and a dark-field signal due to a second fiber bundle by the X-ray imaging apparatus according to one embodiment, wherein (a) of FIG. 7 is a diagram of the case of (a) of FIG. 2, and (b) of FIG. 7 is a diagram of the case of (a) of FIG. 3 (with no scattering correction).

Figure 8:
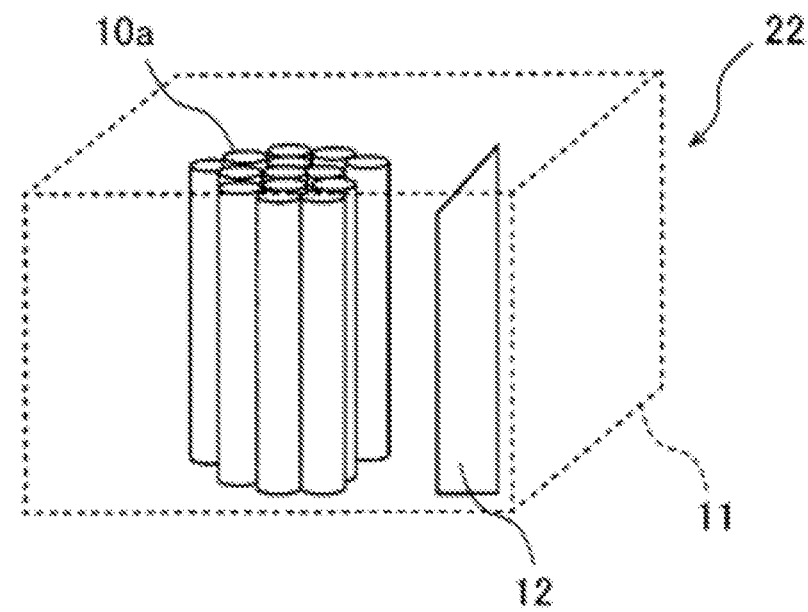

FIG. 8 is three-dimensional dark-field data generated by performing a scattering correction and reconstruction on the dark-field image generated by the X-ray imaging apparatus of (a) of FIG. 3.

Figure 9:
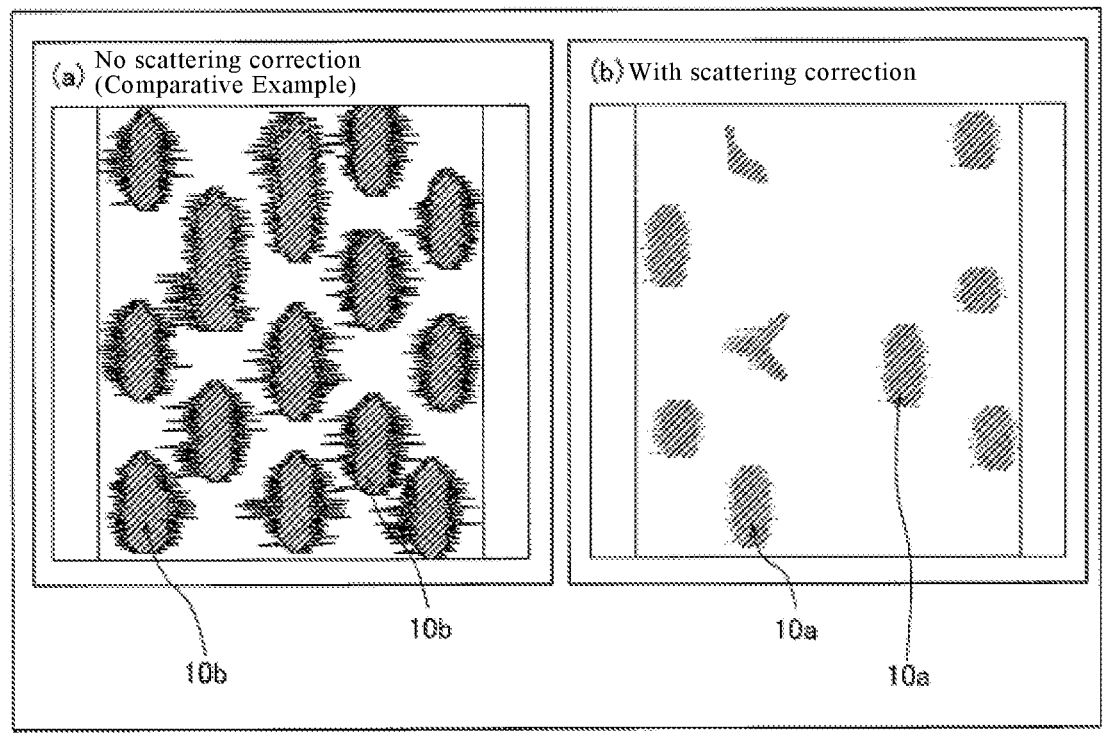

FIG. 9 is a cross-sectional image of three-dimensional dark-field data by the X-ray imaging apparatus according to one embodiment, wherein (a) of FIG. 9 is a cross-sectional image Comparative Example of (b) of FIG. 3, and (b) of FIG. 9 is a cross-sectional image of FIG. 8.

Figure 10:
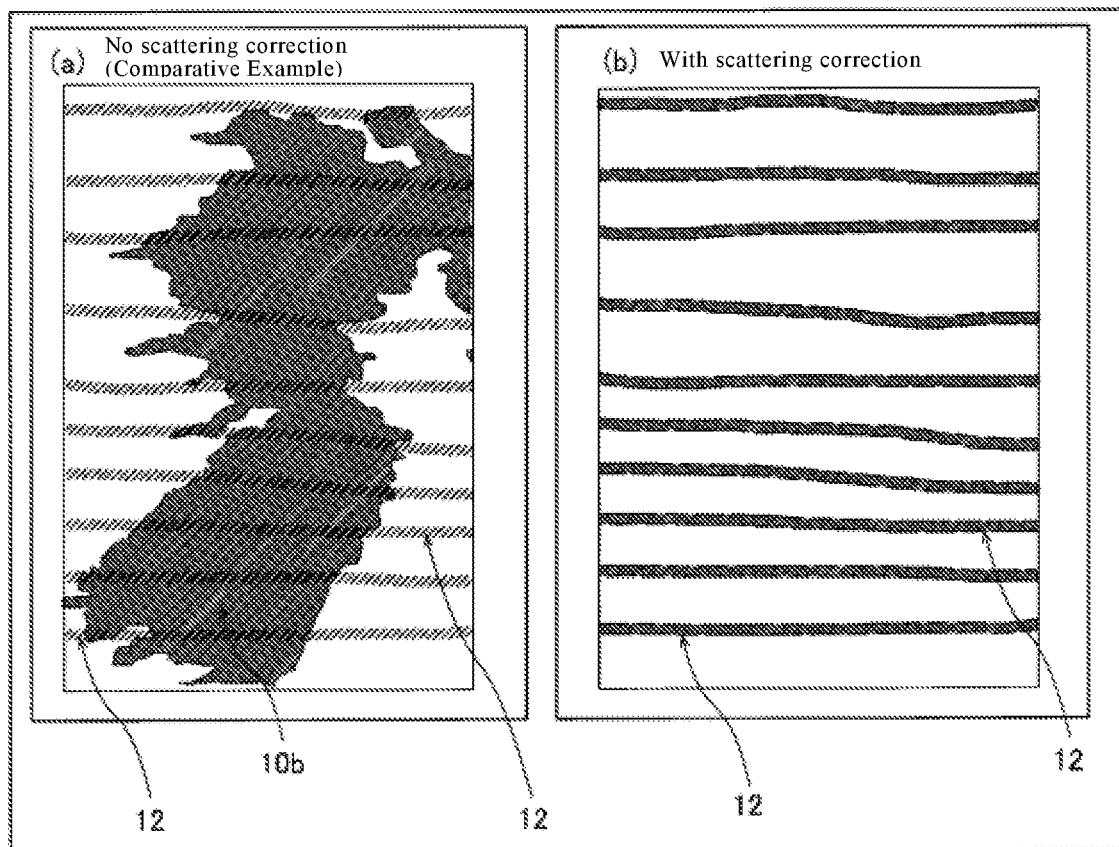

FIG. 10 is a cross-sectional image of three-dimensional dark-field data (generated using a subject other than that of FIG. 9) by the X-ray imaging apparatus according to an embodiment, wherein (a) of FIG. 10 is a cross-sectional image (Comparative Example) of (b) of FIG. 3, and (b) of FIG. 10 is a cross-sectional image of FIG. 8.

Figure 11:
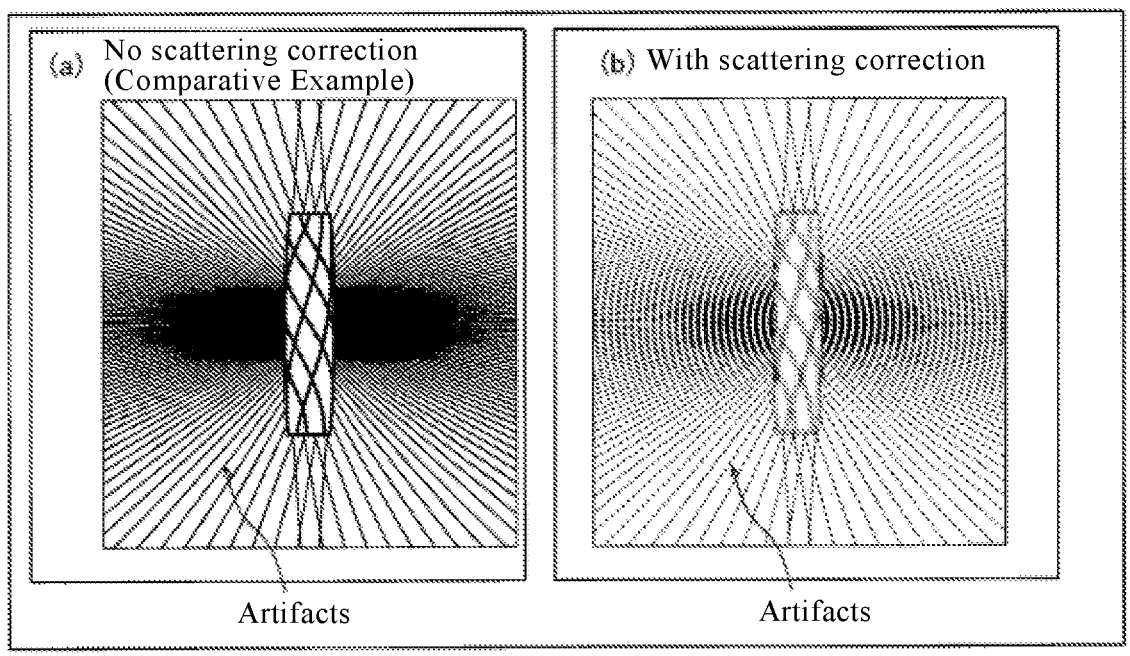

FIG. 11 is a cross-sectional image of three-dimensional dark-field data (along a direction different from that of FIG. 10) by the X-ray imaging apparatus according to one embodiment, wherein (a) of FIG. 11 is a cross-sectional image (Comparative Example) of (b) of FIG. 3, and (b) of FIG. 11 is a cross-sectional image of FIG. 8.

Figure 12:
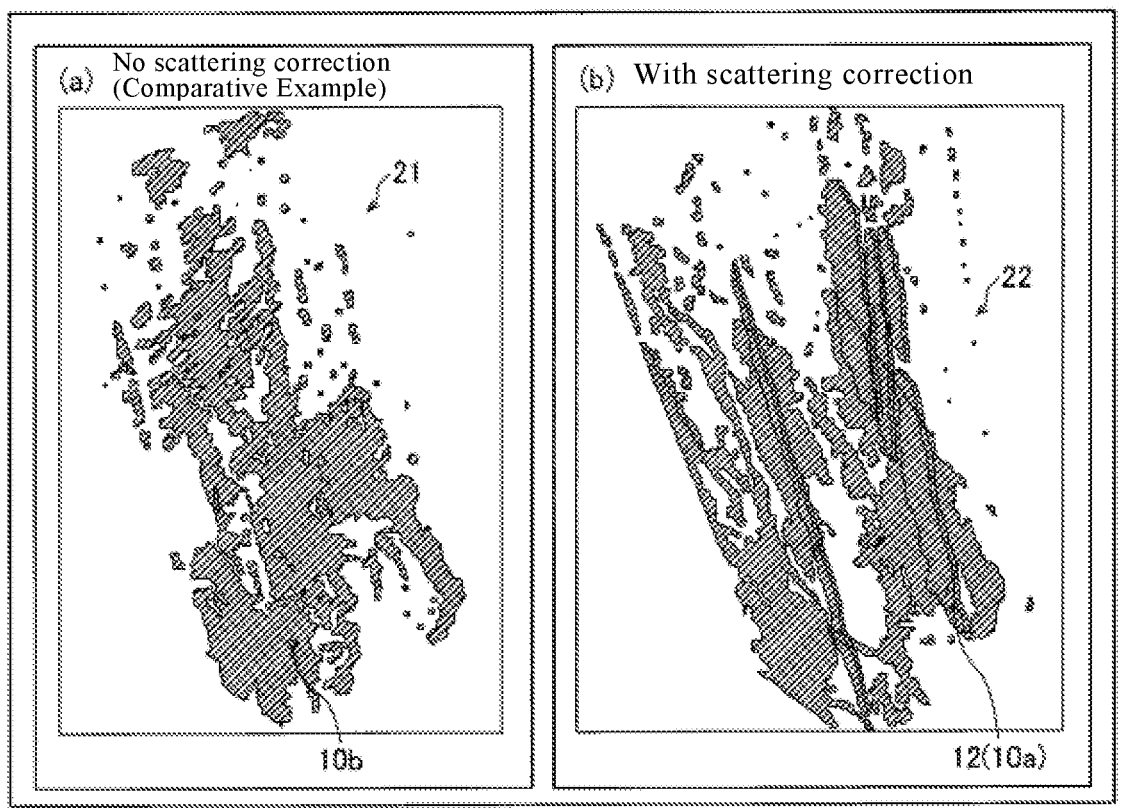

FIG. 12 is a diagram showing three-dimensional dark-field data by the X-ray imaging apparatus according to one embodiment, wherein (a) of FIG. 12 is three-dimensional dark-field data (Comparative Example) shown in (b) of FIG. 3, and (b) of FIG. 12 is a three-dimensional dark-field data shown in FIG. 8.

Figure 13:
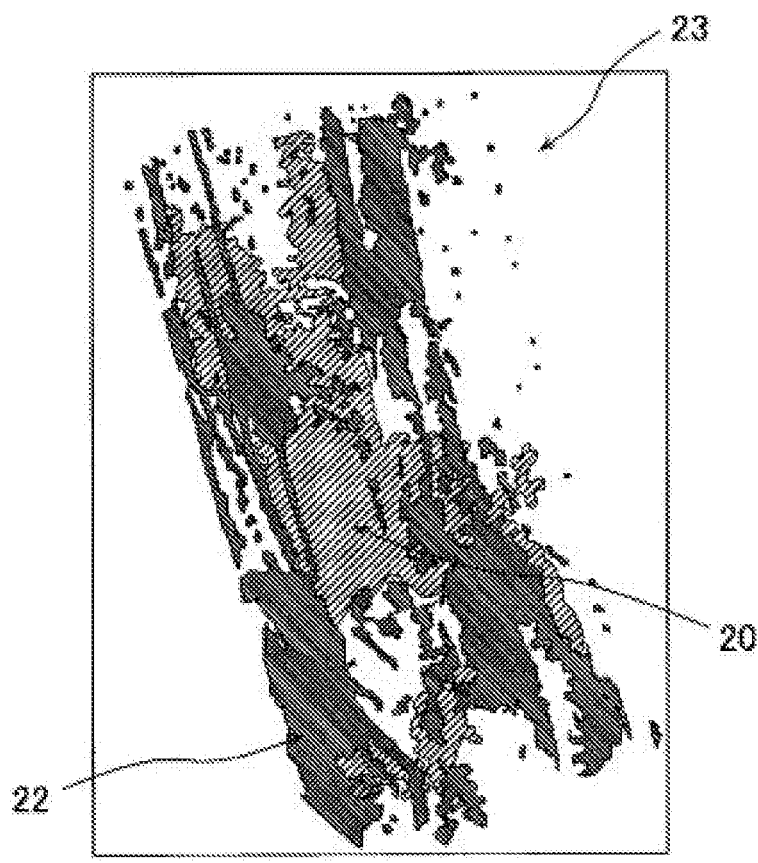

FIG. 13 is a diagram showing a three-dimensional image obtained by combining three-dimensional dark-field data shown in FIG. 8 and three-dimensional dark-field data shown in (b) of FIG. 2 by the X-ray imaging apparatus according to one embodiment.

Figure 14:
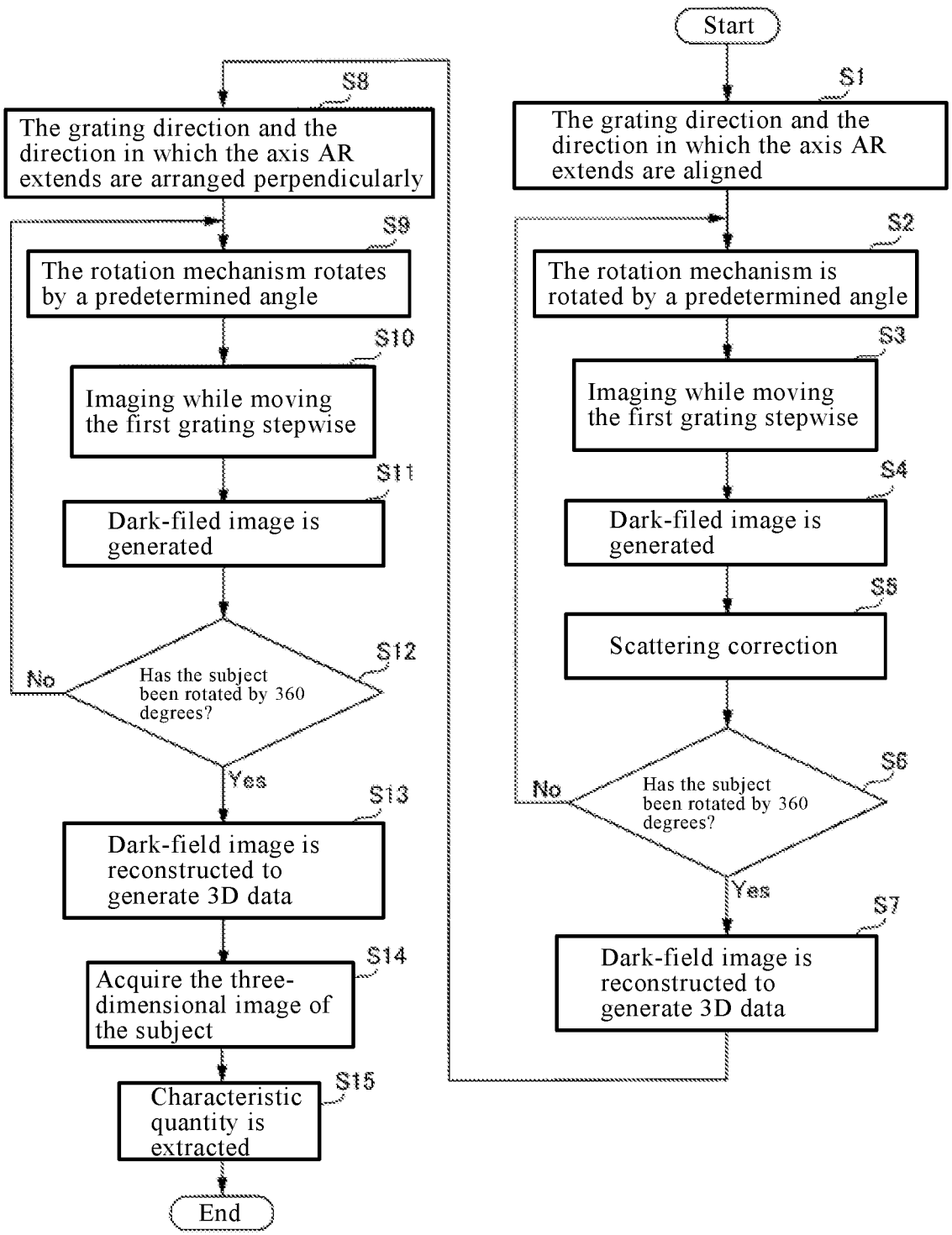

FIG. 14 is a flowchart for explaining an imaging method by the X-ray imaging apparatus according to one embodiment.

EMBODIMENTS FOR CARRYING OUT THE INVENTION

Hereinafter, embodiments in which the present invention is embodied will be described with reference to the attached drawings.

This Embodiment

With reference to FIG. 1 to FIG. 14, the configuration of an X-ray imaging apparatus 100 according to this embodiment will be described.

(Configuration of X-ray Imaging Apparatus)

Figure 1:
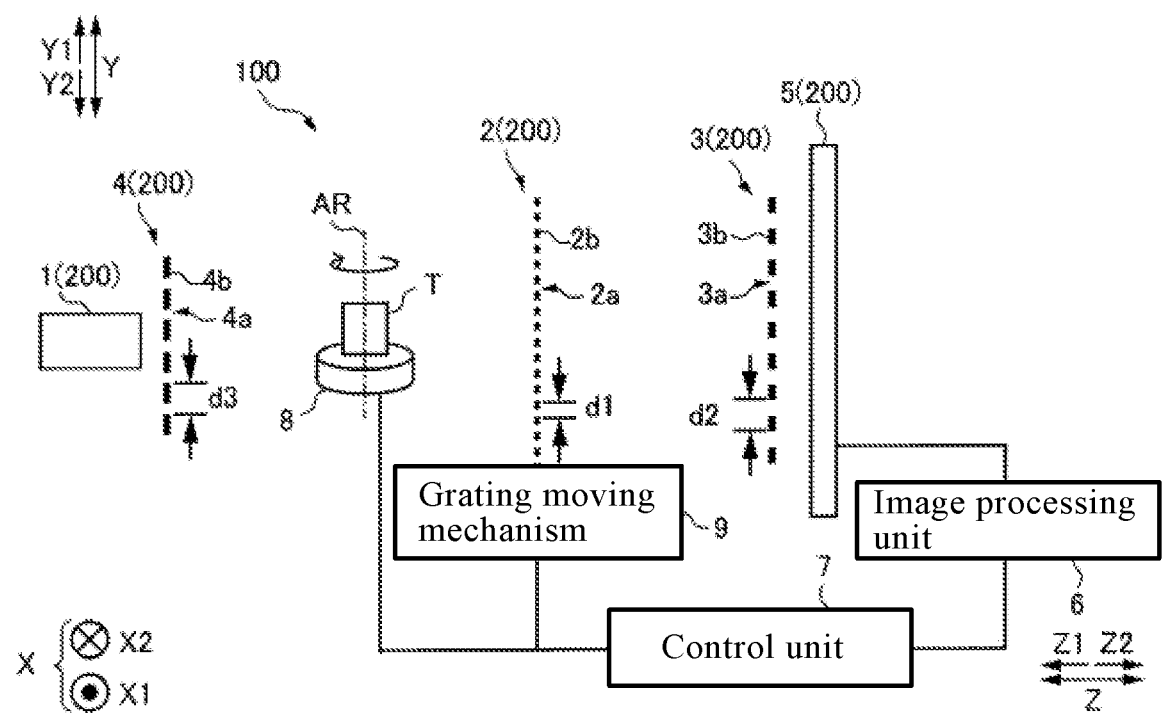
FIG. 1 is a schematic diagram showing a configuration of an X-ray imaging apparatus according to an embodiment.

As shown in FIG. 1, the X-ray imaging apparatus 100 is an apparatus for imaging an inside of a subject T using diffusion (scattering) of X-rays that have passed through the subject T. The X-ray imaging apparatus 100 is an apparatus for imaging an inside of a subject T using a Talbot effect. For example, in a non-destructive testing application, the X-ray imaging apparatus 100 can be used for imaging an inside of an object.

The subject T includes a fiber bundle 10 (see FIG. 2) therein. The subject T is, for example, a carbon fiber reinforced plastic (CFRP) in which carbon fibers are used as a fiber bundle 10 and a resin 11 (see FIG. 2) is used as the base material. The fiber bundle is a bundle of a plurality of fibers. In this embodiment, the fiber bundle 10 is formed in a plate shape by a large number of fibers.

FIG. 1 is a view of the X-ray imaging apparatus 100 as viewed in the X-direction. As shown in FIG. 1, the X-ray imaging apparatus 100 is provided with an X-ray source 1, a first grating 2, a second grating 3, a third grating 4, a detector 5, an image processing unit 6, a control unit 7, a rotation mechanism 8, and a grating moving mechanism 9. In this specification, the direction from the X-ray source 1 to the first grating 2 is referred to as a Z2-direction, and the opposite direction is referred to as a Z1-direction. The left-right direction in a plane orthogonal to the Z-direction is defined as an X-direction, the direction toward the back side of the paper is defined as an X2-direction, and the direction toward the front side of the paper is defined as an X1-direction. The up-down direction in a plane orthogonal to the Z-direction is defined as a Y-direction, the upward direction is defined as a Y1-direction, and the downward direction is defined as a Y2-direction.

The X-ray source 1 is configured to generate X-rays by applying a high voltage, and to emit the generated X-rays in the Z2-direction.

The first grating 2 has a plurality of slits 2a arranged in the Y-direction at a predetermined period (pitch) d1 and X-ray phase-change parts 2b. Each slit 2a and each X-ray phase-change part 2b are formed so as to extend linearly. Each slit 2a and each X-ray phase-change part 2b are formed so as to extend in parallel with each other. The first grating 2 is a so-called phase grating. Note that the X-ray phase-change part 2b is an example of the "first grating structure part" recited in claims.

The first grating 2 is arranged between the X-ray source 1 and the second grating 3, and is irradiated with X-rays from the X-ray source 1. The first grating 2 is provided to form a self-image (not shown) of the first grating 2 by a Talbot effect. Note that when X-rays having a coherence pass through a grating in which slits are formed, an image (self-image) of the grating is formed at a predetermined distance (a Talbot distance) from the grating. This is called a Talbot effect.

The second grating 3 has a plurality of X-ray transmission part 3a and X-ray absorption parts 3b arranged at a predetermined period (pitch) d2 in the Y-direction. The X-ray absorption parts 3b extend along the direction along which the X-ray phase-change parts 2b extend. Each X-ray transmission part 3a and each X-ray absorption part 3b are formed so as to extend linearly. Each X-ray transmission part 3a and each X-ray absorption part 3b are formed so as to extend in parallel with each other. The second grating 3 is a so-called absorbing grating. The first grating 2 and the second grating 3 are gratings with distinct roles, but the slit 2a and the X-ray transmission part 3a each allow X-rays to pass through. Further, the X-ray absorption part 3b functions to shield the X-rays, and the X-ray phase-change part 2b changes the phase of the X-rays according to the difference in the refractive index between the slit 2a and the X-ray phase-change part. Note that the X-ray absorption part 3b is an example of the "second grating structure part" recited in claims.

The second grating 3 is arranged between the first grating 2 and the detector 5, and is irradiated with X-rays that have passed through the first grating 2. The second grating 3 is arranged at a position apart from the first grating 2 by the Talbot distance. The second grating 3 interferes with the self-image of the first grating 2 to form a moiré fringe (not shown) on the sensing surface of the detector 5.

The third grating 4 has a plurality of X-ray transmission parts 4a and X-ray absorption parts 4b arranged in the Y-direction at a predetermined period (pitch) d3. Each X-ray transmission part 4a and each X-ray absorption part 4b are formed so as to extend linearly. Each X-ray transmission part 4a and each X-ray absorption part 4b are formed so as to extend in parallel with each other. The third grating 4 is a so-called multi slit.

The third grating 4 is arranged between the X-ray source 1 and the first grating 2. The third grating 4 is configured to convert the X-rays from the X-ray source 1 into a multipoint light source by using the X-rays that have passed through the respective X-ray transmission parts 4a as a line light source. When the pitches of the three sheets of gratings (the first grating 2, the second grating 3, and the third grating 4) and the distance between gratings satisfy a certain condition, the coherence of the X-rays emitted from the X-ray source 1 can be enhanced. As a result, even if the focal size of the X-ray source 1 of the X-ray tube is large, the interference intensity can be maintained.

The detector 5 is configured to detect X-rays, convert the detected X-rays into an electrical signal, and read the converted electrical signal as an image signal. The detector 5 is, for example, an FPD (Flat Panel Detector). The detector 5 is composed of a plurality of conversion elements (not shown) and pixel electrodes (not shown) arranged on the plurality of conversion elements. The plurality of converting elements and the plurality of pixel electrodes are arranged in an array in the X-direction and the Y-direction at a predetermined period (pixel pitch). The detector 5 is configured to output the acquired image signal to the image processing unit 6.

The image processing unit 6 is configured to generate an absorption image (not shown) based on the image signals output from the detector 5. The image processing unit 6 is configured to generate a dark-field image (see FIG. 5) based on the intensity distribution of the X-rays detected by the detector 5. Here, the absorption image is an image obtained by imaging the contrast generated by the difference in the X-ray absorption by the subject T. The dark-field image is an image obtained by imaging the contrast generated by the refraction of the X-rays by the microstructure inside the subject T. The image processing unit 6 generates a three-dimensional absorption image (not shown) and a three-dimensional dark-field image (see (b) of FIG. 2, etc.) by reconstructing a plurality of absorption images and a plurality of dark-field images captured (at each of a plurality of rotation angles) while rotating the rotation mechanism 8. The image processing unit 6 includes a processor, such as, e.g., a GPU (Graphics Processing Unit) and an FPGA (Field-Programmable Gate Array) configured for image processing.

The control unit 7 is configured to relatively rotate the subject T and an imaging system 200 composed of the X-ray source 1, the detector 5, and the plurality of gratings (the first grating 2, the second grating 3, and the third grating 4) via a rotation mechanism 8. The control unit 7 is configured to move the first grating 2 stepwise in a grating plane in a direction perpendicular to the grating direction through the grating moving mechanism 9. In the X-ray imaging apparatus 100, a technique (fringe scanning method) of acquiring a reconstructed image from a plurality of moiré fringes (images) obtained by scanning a first grating 2 at regular intervals is used. The control unit 7 includes, for example, a processor such as a CPU (Central Processing Unit). Note that the grating direction is an example of the "direction in which each of the first grating structure part and the second grating structure part extends" recited in claims.

The rotation mechanism 8 is configured to relatively rotate the subject T and the imaging system 200 based on the signal from the control unit 7. Specifically, the rotation mechanism 8 is configured to rotate the subject T relative to the imaging system 200 by rotating the subject T about the axis AR. Although FIG. 1 illustrates a state in which the direction in which the axis AR extends (the Y-direction in FIG. 1) and the grating direction of the plurality of gratings (the X-direction in FIG. 1) are perpendicular to each other, the grating direction of the plurality of gratings can be changed in a predetermined direction (e.g., the Y-direction). Note that the grating direction is a direction in which the grating pattern of the gratings extends. The grating pattern refers to the slit 2a, the X-ray phase-change part 2b, the X-ray transmission part 3a, the X-ray absorption part 3b, and the like of the respective gratings. The rotation mechanism 8 includes, for example, a rotary stage driven by a motor and the like. Note that the axis AR is an example of the "rotation axis" recited in claims.

The grating moving mechanism 9 is configured to move the first grating 2 stepwise in a direction (the Y-direction in FIG. 1) perpendicular to the grating direction in the grating plane (the X-Y plane) based on the signal from the control unit 7. Specifically, the grating moving mechanism 9 divides the period d1 of the first grating 2 by n, and moves the first grating 2 stepwise by d1/n. The grating moving mechanism 9 is configured to move the first grating 2 stepwise by at least one period d1 of the first grating 2. Note that "n" is a positive integer, for example, 9. The grating moving mechanism 9 includes, for example, a stepping motor and a piezoelectric actuator.

As shown in (a) of FIG. 2, the fiber bundle 10 includes a fiber bundle 10 extending in a plurality of different directions within the subject T. In the example shown in (a) of FIG. 2, the subject T has a structure in which a fiber bundle 10a extending in a direction (the Y-direction) perpendicular to the grating direction when the first grating 2 and the second grating 3 are viewed from the front (as viewed in the Z-direction) and a fiber bundle 10b extending in the grating direction (the X-direction) are knitted. In the example shown in (a) of FIG. 2, although the fiber bundle 10a and the fiber bundle 10b are shown separately, they are actually carbon fibers of the same type woven (or knitted) into a sheet. Note that the X-direction and the Y-direction are examples of the "direction different from a predetermined direction" and the "predetermined direction" recited in claims, respectively. Also note that the fiber bundle 10a and the fiber bundle 10b are examples of the "first fiber bundle" and the "second fiber bundle" recited in claims, respectively.

In some cases, a crack 12 is formed in the resin 11 of the subject T. In the example shown in FIG. 2, the crack 12 extends in the Y-direction. Note that the crack 12 is an air layer, etc., formed in the resin 11.

In the case shown in FIG. 2, the direction (the Y-direction in (a) of FIG. 2) in which the axis AR extends and the grating direction (the X-direction in (a) of FIG. 2) are perpendicular to each other. In this case, an image of a fiber bundle (fiber bundle 10b in (a) of FIG. 2) extending in the grating direction among the fiber bundle 10 appears in the dark-field image. By reconstructing dark-field images (see the dark-field images 20a to 20d in FIG. 5) at the plurality of rotation angles generated in this case, 3D data 20 (see (b) of FIG. 2) in which the three-dimensional image of the fiber bundle 10b is clearly displayed is generated. Note that the 3D data 20 is an example of the "second three-dimensional dark-field image" recited in claims.

In Comparative Example shown in FIG. 3, the direction in which the axis AR extends (the Y-direction in (a) of FIG. 3) and the grating direction (the Y-direction in (a) of FIG. 3) are aligned. In this case, in addition to the images of the fiber bundle (fiber bundle 10a in (a) of FIG. 3) extending in the grating direction among the fiber bundle 10 and the crack 12, the fiber bundle (the fiber bundle 10b in (a) of FIG. 3) extending in a direction (the X-direction) perpendicular to the grating direction appears in the dark-field image. By reconstructing the dark-field images (see the dark-field images 21b to 21d in FIG. 5) at the plurality of rotation angles generated in this case, 3D data 21 (see (b) of FIG. 3) in which the three-dimensional image of the fiber bundle 10b appears is generated in addition to the three-dimensional image of the fiber bundle 10a and the crack 12.

Here, referring to FIG. 4, the reason why the fiber bundle (the fiber bundle 10b in (a) of FIG. 3) extending in a direction (the X-direction) perpendicular to the grating direction appears in the dark-field image (see the dark-field images 21b to 21d in FIG. 5) when the direction in which the axis AR extends and the grating direction are aligned (see (a) of FIG. 3).

(a) of FIG. 4 is a schematic diagram showing an example in which the fiber bundle 10b of the subject T is arranged perpendicular to the optical axis of the X-rays in the X-Z plane. (b) of FIG. 4 is a cross-sectional view taken along the line 400-400 in (a) of FIG. 4. (c) of FIG. 4 is a schematic diagram showing an example in which the fiber bundle 10b of the subject T is inclined with respect to the optical axis of the X-rays in the X-Z plane. (d) of FIG. 4 is a cross-sectional view taken along the line 500-500 in (c) of FIG. 4.

Here, when the X-rays enter the fiber bundle 10 extending in a direction perpendicular to the optical axis of the X-rays, the X-rays are scattered (diffused) by the fiber bundle 10. Specifically, at the interface between the fibers and the resin 11 in the subject T (see FIG. 2), the X-rays are refracted by the difference in the refractive factor between the fiber and the resin 11. Since the fiber bundle 10 is laminated in the subject T and the fiber bundle 10 is composed of a large number of fibers, when the X-rays pass through a large number of fibers, multiple refractions occur. Thus, the X-rays are scattered (diffused).

In the example shown in (a) of FIG. 4, the fiber bundle 10b is arranged perpendicular to the optical axis of the X-rays. That is, the fiber bundle 10b is arranged to extend in the X-direction. Therefore, as shown in (b) of FIG. 4, the cross-section of the fiber is substantially circular. In the example shown in (c) of FIG. 4, the fiber bundle 10b is arranged obliquely with respect to the optical axis of the X-rays. Therefore, as shown in (d) of FIG. 4, the cross-section of the fiber is elliptical. When the cross-section of the fiber is elliptical, the distance that the X-rays pass through the interface between the fiber and the resin 11 is longer as compared with the case in which the cross-section of the fiber is substantially circular. In addition, the interface between the fiber and the resin 11 has a rough shape (minute irregularities), and the scattering (diffusion) of the X-rays increases as the distance that the X-rays pass through the interface between the fiber and the resin 11 increases.

FIG. 5 is a schematic diagrams (a) to (d) showing dark-field images 20a to 20d when the direction in which the axis AR extends and the grating direction are perpendicular to each other (see FIG. 2) and dark-field images 21a to 21d when the direction in which the axis AR extends and the grating direction are aligned (see FIG. 3) at certain angles (first angle $\theta_1$, second angle $\theta_2$, third angle $\theta_3$, and fourth angle $\theta_4$) when imaging is performed while rotating the subject T in the X-ray imaging apparatus 100 according to this embodiment.

When the direction in which the axis AR extends and the grating direction are perpendicular to each other, the fiber bundle 10b appears clearly in the dark-field image (the dark-field image 20a) at the first angle $\theta_1$ (see (a) of FIG. 5). Also, in the dark-field image (the dark-field images 20b to 20d) with a relatively large angle (see (b) to (d) of FIG. 5), as the angle increases, the scatterin (diffusion) (see FIG. 4) of the X-rays by the fiber bundle 10b increases. As a result, the dark-field signal (see the solid line in (a) of FIG. 7) of the bundle 10b becomes large. In this case, since the scattering (diffusion) of the X-rays by the fiber bundle 10a does not change greatly even when the angle becomes large, the dark-field signal (see the broken line in (a) of FIG. 7) of the fiber bundle 10a (and the crack 12) does not become large. Here, the dark-field signal is a value obtained by f(1/V) when a pixel value of a predetermined pixel in a dark-field image is V. The function f(x) is a function whose value increases as the value of the argument x increases. Therefore, when the X-ray scattering intensity is large and the pixel value (brightness) of the dark-field image is small (that is, when V is large), the dark-field signal is large. Note that the dark-field signal is an example of the "value based on the X-ray scattering intensity" recited in claims.

On the other hand, when the direction in which the axis AR extends and the grating direction are aligned, in the dark-field image (the dark-field image 21a) at the first angle θ₁ having a relatively small angle, the dark-field signal (see the solid line in (b) of FIG. 7) of the fiber bundle 10b is relatively small and the fiber bundle 10a (and the crack 12) appears clearly. However, as the angle increases, the scattering (diffusion) of the X-rays by the fiber bundle 10b increases, so that the dark-field signal (see the solid line in (b) of FIG. 7) of the fiber bundle 10b increases with respect to the dark-field signal (see the broken line in (b) of FIG. 7) of the fiber bundle 10a. For this reason, the image of the fiber bundle 10b appears remarkably in the dark-field images 21b to 21d. Therefore, it becomes difficult to grasp the detailed structure of the fiber bundle 10a (and the crack 12).

FIG. 6 is a sinogram captured while rotating the subject T by 360 degrees in the X-ray imaging apparatus 100 according to this embodiment. The sinogram of FIG. 6 shows outputs of the detector 5 at each of a plurality of rotation angles. As shown in each of the sinogram (see (a) of FIG. 6) in the case where the direction in which the axis AR extends and the grating direction are perpendicular to each other, and the sinogram (see (b) of FIG. 6) in the case where the direction in which the axis AR extends and the grating direction are aligned with each other, it can be seen that scattering (diffusion) of the X-rays by the fiber bundle 10b is increased at predetermined rotation angles (see hatched portions in (a) of FIG. 6 and (b) of FIG. 6). That is, the shaded portions of (a) of FIG. 6 and (b) of FIG. 6 correspond to rotation angles (see solid lines in (a) and (b) of FIG. 7) relatively large in the dark-field signal.

Here, in this embodiment, the image processing unit 6 (see FIG. 1) is configured to perform a scattering correction for reducing the dark-field signal of a pixel in which the dark-field signal is larger than a threshold value V1 (see (b) of FIG. 7) among the plurality of pixels in the dark-field image to a set value V2. In this embodiment, the set value V2 is equal to the threshold value V1. Note that the threshold value V1 and the set value V2 are examples of the "predetermined threshold value" and the "predetermined set value" recited in claims, respectively.

Specifically, the image processing unit 6 performs a scattering correction on each of a plurality of pixels included in the dark-field image. Specifically, the image processing unit 6 reduces the dark-field signal of the pixel whose dark-field signal is larger than the threshold value V1 among a plurality of pieces of pixels included in the dark-field image to the set value V2 (threshold value V1) by the scattering correction. In addition, the image processing unit 6 does not perform a scattering correction on a pixel whose dark-field signal is equal to or less than the threshold value V1 among a plurality of pieces of pixels included in the dark-field image, and does not change the dark-field signal.

Further, in this embodiment, the image processing unit 6 is configured to perform a scattering correction on the dark-field image of the subject T including the fiber bundle 10 when the direction in which the axis AR extends and the grating direction are aligned (see (a) of FIG. 3). Specifically, the image processing unit 6 performs a scattering correction on dark-field images (see dark-field images 21a to 21d in FIG. 5) at each of the plurality of rotation angles when the direction in which the axis AR extends and the grating direction are aligned.

Then, as shown in FIG. 8, the image processing unit 6 generates 3D data 22 by reconstructing the dark-field image at each of the plurality of rotation angles on which the scattering correction has been performed. Note that the 3D data 22 is an example of the "first three-dimensional dark-field image" recited in claims.

The image processing unit 6 is configured such that a change of whether or not a scattering correction is performed can be accepted. In this embodiment, the image processing unit 6 is configured such that the scattering correction is not performed when the direction in which the axis AR extends and the grating direction are perpendicular to each other (see (a) of FIG. 2).

In this embodiment, the image processing unit 6 is configured to reduce the sum of the dark-field signal (see the solid line in (b) of FIG. 7) due to the fiber bundle 10a and the dark-field signal (see the broken line in (b) of FIG. 7) due to the fiber bundle 10b to the set value V2 (the threshold value V1) by the scattering correction. Note that the set value V2 (threshold value V1) is a value that has been preset by a user.

In this embodiment, the image processing unit 6 is configured to accept a change in the set value V2. Specifically, when the user instructs to change the set value V2 on an operating unit (not shown), the set value V2 of the image processing unit 6 is changed by the control unit 7 (see FIG. 1) based on the user's instruction.

(a) of FIG. 9 is a cross-sectional image (Comparative Example) along a predetermined direction of the 3D data 21 (see (b) of FIG. 3) when no scattering correction is performed in cases where the direction in which the axis AR extends and the grating direction are aligned (see (a) of FIG. 3). (b) of FIG. 9 is a cross-sectional image along a predetermined direction of the 3D data 22 (see FIG. 8) when a scattering correction is performed in the cases where the direction in which the axis AR extends and the grating direction are aligned (see (a) of FIG. 3). In Comparative Example shown in (a) of FIG. 9, the image (hatched portions) of the fiber bundle 10b appears remarkably in the cross-sectional image, and the image of the fiber bundle 10a (and the crack 12) does not appear. On the other hand, in the example shown in (b) FIG. 9, the image of the fiber bundle 10b appearing in (a) of FIG. 9 does not appear, and the image (hatched portion) of the fiber bundle 10a appears remarkably. In the example shown in (b) of FIG. 9, no image of the crack 12 appears.

In the examples shown in FIG. 10, an image of the subject T of a type different from that in FIG. 9 are shown. (a) of FIG. 10 shows a cross-sectional image (Comparative Example) taken along the 3D data 21 (see (b) of FIG. 3 and (a) of FIG. 12) when no scattering correction is performed in cases where the direction in which the axis AR extends and the grating direction are aligned (see (a) of FIG. 3). (b) of FIG. 10 is a cross-sectional image taken along a predetermined direction of the 3D data 22 (see FIG. 8 and (b) of FIG. 12) when a scattering correction is performed in the cases where the direction in which the axis AR extends and the grating direction are aligned (see (a) of FIG. 3). In Comparative Example shown in (a) FIG. 10, the image of the crack 12 (streaky portion) appears in the cross-sectional image, but similarly to (a) of FIG. 9, the image of the fiber bundle 10*b* (hatched portion) appears remarkably, and the image of the crack 12 becomes difficult to visually recognize. On the other hand, in the example shown in (b) of FIG. 10, the image of the fiber bundle 10*b* appeared in (a) of FIG. 10 does not appear, and the image of the crack 12 (hatched portion) appears remarkably. In the example shown in (b) of FIG. 10, the image of the fiber bundle 10*a* does not appear remarkably.

FIG. 11 shows a cross-sectional image taken along a direction different from that of FIG. 10. In Comparative Example shown in (a) of FIG. 11, in the cross-sectional image, artifacts (noises) (radial lines extending outward from the subject T) due to scattering of the X-rays by the fiber bundle 10*b* remarkably appear. Further, in (b) of FIG. 11, generation of artifacts (noises) due to the scattering of the X-rays by the fiber bundle 10*b* is suppressed as compared with Comparative Example of (a) of FIG. 11.

FIG. 12 shows 3D data of the subject T of FIG. 10 and FIG. 11. As shown in (a) of FIG. 12, in the 3D data 21 in which no scattering correction is performed, the three-dimensional image of the fiber bundle 10*b* appears remarkably. As shown in (b) of FIG. 12, in the 3D data 22 in which a scattering correction is performed, the three-dimensional image of the crack 12 (and the fiber bundle 10*a*) appears remarkably.

Here, in this embodiment, as shown in FIG. 13, the image processing unit 6 is configured to generate the 3D data 20 (see (b) of FIG. 2) by reconstructing the dark-field images (see the dark-field images 20*a* to 20*d* in FIG. 5) at each of the plurality of rotation angles without performing a scattering correction in cases where the axis AR extends and the grating direction are substantially perpendicular to each other (see (a) of FIG. 2) when the first grating 2 and the second grating 3 are viewed from the front (viewed in the Z-direction). The image processing unit 6 is configured to combine the 3D data 22 and the 3D data 20 to obtain the three-dimensional image 23 of the subject T. That is, the image processing unit 6 is configured to synthesize the 3D data 22 and the 3D data 20 to obtain (generate) one three-dimensional image 23.

(Imaging of Subject)

Next, with reference to FIG. 14, the flow of the process of capturing an image of a subject T by the X-ray imaging apparatus 100 according to this embodiment will be described.

In Step S1, the grating direction and the direction in which the axis AR extends are aligned. In this case, the fiber bundle 10*a* is provided so as to extend along the grating direction, and the fiber bundle 10*b* is provided so as to extend along a direction perpendicular to the grating direction when the first grating 2 and the second grating 3 are viewed from the front.

Next, in Step S2, the subject T is rotated by a predetermined angle (e.g., one degree) by the control unit 7 through the rotation mechanism 8.

Next, in Step S3, the subject T is imaged while moving the first grating 2 stepwise through the grating moving mechanism 9 by the control unit 7. Next, in Step S4, the dark-field image of the subject T is generated by the image processing unit 6.

Next, in Step S5, a scattering correction is performed by the image processing unit 6 on the dark-field image generated in Step S4.

Next, in Step S6, the control unit 7 determines whether or not the rotation mechanism 8 has rotated the subject T by 360 degrees. If the subject T has not been rotated by 360 degrees, the process returns to Step S2. If the subject T has been rotated by 360 degrees, the process proceeds to Step S7.

In Step S7, the dark-field image captured at each rotation angle is reconstructed by the image processing unit 6, and the three-dimensional data (3D data 22 (see FIG. 8)) of the subject T is generated. In this case, the image processing unit 6 may perform a correcting process including at least a smoothing process on the generated 3D data 22. The smoothing process includes, for example, smoothing by filtering with a Gaussian filter or the like.

Next, in Step S8, the plurality of gratings is rotated so that the grating direction and the direction in which the axis AR extends are perpendicular to each other. In this case, the fiber bundle 10*b* is provided so as to extend along the grating direction, and the fiber bundle 10*a* is provided so as to extend along the direction perpendicular to the grating direction when the first grating 2 and the second grating 3 are viewed from the front.

Next, in Step S9, the subject T is rotated by a predetermined angle (e.g., one degree) by the control unit 7 through the rotation mechanism 8.

Next, in Step S10, the subject T is imaged while moving the first grating 2 stepwise through the grating moving mechanism 9 by the control unit 7. Next, in Step S11, the dark-field image of the subject T is generated by the image processing unit 6.

Next, in Step S12, the control unit 7 determines whether or not the rotation mechanism 8 has rotated the subject T by 360 degrees. If the subject T has not been rotated by 360 degrees, the process returns to Step S9. If the subject T has been rotated by 360 degrees, the process proceeds to Step S13.

In Step S13, the image processing unit 6 reconstructs the dark-field images (see the dark-field images 20*a* to 20*d* in FIG. 5) captured at the respective rotation angles, and generates the three-dimensional data (3D data 20) (see (b) of FIG. 2) of the subject T. In this case, the image processing unit 6 may perform a correcting process including a smoothing process on the generated 3D data 20.

In Step S14, the image processing unit 6 combines (synthesizes) the 3D data 22 generated in Step S7 with the 3D data 20 generated in Step 13 to obtain the three-dimensional image 23 of the subject T.

In Step S15, a predetermined characteristic quantity is extracted from the three-dimensional image 23 acquired in Step S14 by the image processing unit 6. Features extracted in this case include the height of the weave of the fiber bundle 10, the size of the gap between adjacent fiber bundles 10, the width of the fiber bundle 10, the length of the fiber bundle 10, the curvature of the fiber bundle 10, the thickness of the fiber bundle 10, the length of the crack 12, the depth of the crack 12, the number of the cracks 12, and the curvature of the crack 12. Further, the regularity of the knitting of the fiber bundle 10 may be extracted as the characteristic quantity.

Effects of Embodiment

In this embodiment, the following effects can be obtained.

In this embodiment, as described above, the X-ray imaging apparatus 100 is configured such that the image processing unit 6 performs a scattering correction for reducing the dark-field signal of the pixel whose dark-filed signal is larger than the threshold value V1 among the plurality of pixels in the dark-field image to the set value V2 (threshold value V1). Thus, even if the dark-field signal does not change exponentially with respect to the transmission length (of the X-rays) that changes in response to the rotation angle prior to the scattering correction, the change with respect to the rotation angle (transmission length) of the dark-field signal can be approximated to the exponential change by appropriating the set value V2 in the scattering correction to reduce the dark-field signal to an appropriate value. As a result, it is possible to suppress the generation of artifacts (noises) due to the large X-ray scattering angle, and to suppress blurring of the reconstructed image of the subject T.

In this embodiment, as described above, the image processing unit 6 configures the X-ray imaging apparatus 100 so that the dark-field signal of the pixel whose dark-field signal is larger than the threshold value V1 in the scattering correction is set to the threshold value V1. As a result, it is possible to suppress an increase in the work load required for the user to determine the set value V2 as compared with a case in which the set value V2 and the threshold value V1 are set to separate values.

Further, in this embodiment, as described above, the X-ray imaging apparatus 100 is configured such that the image processing unit 6 performs a scattering correction on the dark-field image of the subject T including the fiber bundle 10 in cases where the direction in which the axis AR of the rotation mechanism 8 extends and the grating direction are aligned. Here, generally, in a dark-field image, the fiber bundle 10 extending along the grating direction appears remarkably. However, in cases where the direction in which the axis AR of the rotation mechanism 8 extends and the grating direction are aligned, in addition to the fiber bundle 10 extending along the grating direction, the fiber bundle 10 extending in a direction perpendicular to the grating direction appears. This is because, depending on the rotation angle, the transmission length of the X-rays with respect to the fiber bundle 10 extending in a direction perpendicular to the grating direction becomes longer (angles) based on the subject T being rotated by the rotation mechanism 8. Therefore, the X-ray scattering angle by the fiber bundle 10 extending in a direction perpendicular to the grating direction becomes large. Therefore, in cases where the direction in which the axis AR of the rotation mechanism 8 extends and the grating direction are aligned, by performing a scattering correction on the dark-field image of the subject T including the fiber bundle 10, it is possible to more effectively suppress the generation of artifacts (noises) due to the scattering of the X-rays by the fiber bundle 10 extending in the direction perpendicular to the grating direction. As a result, blurring of the reconstructed image of the subject T can be more effectively suppressed.

In this embodiment, as described above, the X-ray imaging apparatus 100 is configured such that the image processing unit 6 reduces the sum of the dark-field signal due to the fiber bundle 10a and the dark-field signal due to the fiber bundle 10b to the set value V2 (threshold value V1) by a scattering correction. This makes it possible to control the dark-field signal by a single scattering correction, unlike when the dark-field signal due to the fiber bundle 10a and the dark-field signal due to the fiber bundle 10b are separately reduced by a scattering correction. As a result, it is possible to suppress the time required for the scattering correction from becoming longer.

Further, in this embodiment, as described above, the X-ray imaging apparatus 100 is configured such that one of the fiber bundle 10a and the fiber bundle 10b is provided so as to extend along the grating direction, and the other of the fiber bundle 10a and the fiber bundle 10b is provided so as to extend along a direction perpendicular to the grating direction when the first grating 2 and the second grating 3 are viewed from the front. As a result, it is possible to suppress generation of artifacts (noises) due to the scattering of X-rays by one of the fiber bundle 10a and the fiber bundle 10b extending in the direction perpendicular to the grating direction by the scattering correction. As a result, it is possible to suppress blurring of the other image of the fiber bundle 10a and the fiber bundle 10b extending along the grating direction.

Further, in this embodiment, as described above, the X-ray imaging apparatus 100 is configured such that the image processing unit 6 generates the 3D data 22 by performing the scattering correction on the dark-field images at each of the plurality of rotation angles and reconstructing the dark-field images at each of the plurality of rotation angles on which the scattering correction has been performed when the direction in which the axis AR of the rotation mechanism 8 extends and the grating direction are aligned. As a result, at each of the plurality of rotation angles, the dark-field signal can be made close to the change of the exponential attenuation, so that it is possible to suppress blurring of the 3D data 22.

Further, in this embodiment, as described above, in cases where the direction in which the axis AR extends and the grating direction are substantially perpendicular to each other when the first grating 2 and the second grating 3 are viewed from the front, the X-ray imaging apparatus 100 is configured to generate the 3D data 20 by reconstructing without performing the scattering correction on the dark-field image at each of the plurality of rotation angles and acquire the three-dimensional image 23 of the subject T by combining the 3D data 22 and the 3D data 20. Here, generally, in a dark-field image, in cases where a direction in which the axis AR extends and the grating direction are substantially perpendicular to each other when the first grating 2 and the second grating 3 are viewed from the front, the fiber bundle 10 extending along the grating direction appears remarkably in the dark-field image. This is because, when the subject T is rotated by the rotation mechanism 8, the transmission length of the X-ray does not change greatly by the rotation angle because there is dark field sensitivity to the fiber bundle 10 at any rotation angle with respect to the fiber bundle 10 extending in the direction perpendicular to the grating direction (direction along the axis AR). This results in the fiber bundle 10 in which the fiber bundle 10 displayed prominently in the 3D data 20 and the fiber bundle 10 displayed prominently in the 3D data 22 differ from each other. Therefore, by combining the 3D data 20 and the 3D data 22, the user can visually recognize the positional relation between the fiber bundle 10 which is remarkably displayed on the 3D data 20 and the fiber bundle 10 which is remarkably displayed on the 3D data 22 in the three-dimensional image 23.

Further, in this embodiment, as described above, the X-ray imaging apparatus 100 is configured so that the image processing unit 6 can accept the change of the set value V2. As a result, the set value V2 can be changed according to the type of the subject T, so that the scattering correction can be performed more appropriately.

(Modifications)

It should be noted that the embodiment disclosed herein is to be considered in all respects as illustrative and not restrictive. The scope of the present invention is indicated by the appended claims rather than by the foregoing embodiment descriptions, and includes all modifications (changes) within the meanings and the ranges equivalent to the scope of the claims.

For example, in the aforementioned embodiment, an example is shown in which the scattering correction is performed based on the size of the dark-field signal of the dark-field image, but the present invention is not limited thereto. For example, the scattering correction may be performed based on the pixel value of the dark-field image. Here, when the X-ray scattering is large, the pixel value (brightness) of the dark-field image becomes small. Thus, when performing the scattering correction based on the pixel value, the image processing unit 6 is configured to perform the scattering correction when the pixel value is less than a predetermined threshold value. Here, the pixel value is the "value based on the of X-ray scattering intensity" recited in claims.

In the aforementioned embodiment, although an example is shown in which the predetermined set value (the set value V2) and the predetermined threshold value (the threshold value V1) are equal to each other, the present invention is not limited to this. For example, the predetermined set value (the set value V2) and the predetermined threshold value (the threshold value V1) may be different from each other. In this case, the image processing unit 6 may be configured to estimate an optimal value as the predetermined set value (the set value V2) based on the generated dark-field image.

In the above embodiment, an example is shown in which the scattering correction is performed when the direction in which the rotation axis (the axis AR) of the rotation mechanism 8 extends and the direction (grating direction) in which each of the first grating structure part (the X-ray phase-change part 2b) and the second grating structure part (the X-ray absorption part 3b) extends are the same, but the present invention is not limited to this. For example, the scattering correction may be performed when the direction in which the rotation axis (the axis AR) of rotation mechanism 8 extends and the direction (grating direction) in which each of the first grating structure part (the X-ray phase-change part 2b) and the second grating structure part (the X-ray absorption part 3b) extends are offset by a predetermined angle (e.g., 10 degrees).

In the aforementioned embodiment, although an example is shown in which the first fiber bundle (the fiber bundle 10a) and the second fiber bundle (the fiber bundle 10b) are substantially perpendicular to each other, the present invention is not limited to this. For example, the first fiber bundle (the fiber bundle 10a) and the second fiber bundle (the fiber bundle 10b) may cross each other without being crossed perpendicularly.

In the aforementioned embodiment, an example is shown in which the scattering correction is not performed in generating the second three-dimensional dark-field data (3D data 20), but the present invention is not limited to this. For example, the scattering correction may be performed in generating the second three-dimensional dark-field data (the 3D data 20).

In the aforementioned embodiment, an example is shown in which the second three-dimensional dark-field data (the 3D data 20) is generated after the first three-dimensional dark-field data (the 3D data 22) is generated, but the present invention is not limited to this. For example, the first three-dimensional dark-field data (the 3D data 22) may be generated after the second three-dimensional dark-field data (the 3D data 20) is generated.

In the above embodiment, an example is shown in which the image processing unit 6 combines (synthesizes) the first three-dimensional dark-field data (the 3D data 22) and the second three-dimensional dark-field data (the 3D data 20), but the present invention is not limited to this. For example, in addition to the first three-dimensional dark-field data (the 3D data 22) and the second three-dimensional dark-field data (the 3D data 20), the three-dimensional dark-field data may be combined when the direction in which the rotation axis (the axis AR) extends and the direction in which the first grating structure part (the X-ray phase-change part 2b) and the second grating structure part (the X-ray absorption part 3b) extend (the grating direction) do not intersect at a right angle.

In the aforementioned embodiment, an example is shown in which the third grating 4 is provided, but the present invention is not limited to this. No third grating 4 may be provided.

In the aforementioned embodiment, an example is shown in which the dark-field image is generated by the fringe scan method, but the present invention is not limited to this. For example, the dark-field image may be generated by a method in which either the first grating 2, the second grating 3, or the third grating 4 is rotated in a plane perpendicular to the optical axis direction of the X-rays, that is, a so-called moiré one-shot method.

In the aforementioned embodiment, an example is shown in which the first grating 2 is a phase grating, but the present invention is not limited to this. For example, the first grating 2 may be an absorption grating.

In the aforementioned embodiment, an example is shown in which the rotation mechanism 8 rotates the subject T relative to the imaging system by rotating the subject T, but the present invention is not limited to this. For example, it may be configured to rotate the subject T relative to the imaging system by the rotating imaging system.

In the aforementioned embodiment, an example is shown in which the grating direction of the plurality of gratings and the direction of the subject T are relatively changed by rotating the plurality of gratings, but the present invention is not limited to this. For example, the grating direction of the plurality of gratings and the direction of the subject T may be relatively changed by rotating the subject T.

In the aforementioned embodiment, an example is shown in which the first grating 2 is moved stepwise in a grating plane, but the present invention is not limited to this. Any grating of the plurality of gratings may be moved stepwise.

In the aforementioned embodiment, an example is shown in which an image of carbon-fiber-reinforced plastics (CFRP) is captured as the subject T, but the present invention is not limited to this. For example, a fiberglass reinforced plastic (GFRP) or the like may be used as the subject T. Any subject may be used as long as a fiber bundle is included in a subject to be imaged.

DESCRIPTION OF SYMBOLS

1: X-ray source
2: first grating
2b: X-ray phase-change part (first grating structure part)
3: second grating
3b: X-ray absorption part (second grating structure part)
5: detector
6: image processing unit
8: rotation mechanism
10; fiber bundle
10a: fiber bundle (first fiber bundle)
10b: fiber bundle (second fiber bundle)
20: 3D data (second three-dimensional dark-field data)

20a, 20b, 20c, 20d: dark-field image (dark-filed image when the direction in which the rotation axis extends and the direction in which the first grating structure part and the second grating structure part extend are substantially orthogonal)
21a, 21b, 21c, 21d: dark-field image (dark-filed image when the direction in which the rotation axis extends and the direction in which the first grating structure part and the second grating structure part extend are aligned)
22: 3D data (first three-dimensional dark-field data)
23: three-dimensional image
100: X-ray imaging apparatus
200: imaging system
AR: axis (rotation axis)
T: subject
V1: threshold value (predetermined threshold value)
V2: set value (predetermined set value)

The invention claimed is:

1. An X-ray imaging apparatus comprising:
an X-ray source;
a detector configured to detect X-rays emitted from the X-ray source;
a plurality of gratings arranged between the X-ray source and the detector, the plurality of gratings including a first grating and a second grating;
a rotation mechanism configured to rotate a subject and an imaging system relatively to each other, the imaging system including the X-ray source, the detector, and the plurality of gratings; and
an image processing unit configured to generate a dark-field image as a result of X-ray scattering based on an intensity distribution of the X-rays detected by the detector at each of a plurality of relative rotation angles of the subject and the imaging system resulting from the relative rotation generated by the rotation mechanism,
wherein the image processing unit is configured to perform a scattering correction on one or more targeted pixels included in the dark-field image, the targeted pixels having values related to X-ray scattering intensity, the scattering correction being such that the values of the targeted pixels are reduced to a predetermined set value.

2. The X-ray imaging apparatus as recited in claim 1, wherein the image processing unit is configured to set, in the scattering correction, the value based on the X-ray scattering intensity of the pixel in which the value based on the X-ray scattering intensity is larger than the predetermined threshold value to the predetermined threshold value.

3. The X-ray imaging apparatus as recited in claim 1, wherein the subject includes a fiber bundle,
wherein the first grating includes a first grating structure part,
wherein the second grating includes a second grating structure part extending along a direction in which the first grating structure part extends, and
wherein the image processing unit is configured to perform the scattering correction on the dark-field image of the subject including the fiber bundle in cases where a direction in which a rotation axis of the rotation mechanism extends and a direction in which each of the first grating structure part and the second grating structure part extends are aligned.

4. The X-ray imaging apparatus as recited in claim 3, wherein the fiber bundle includes a first fiber bundle extending in a predetermined direction and a second fiber bundle extending in a direction different from the predetermined direction, and
wherein the image processing unit is configured to reduce a sum of a value based on X-ray scattering intensity due to the first fiber bundle and a value based on the X-ray scattering intensity due to the second fiber bundle to the predetermined set value by the scattering correction.

5. The X-ray imaging apparatus as recited in claim 4, wherein one of the first fiber bundle and the second fiber bundle is provided so as to extend along a direction in which each of the first grating structure part and the second grating structure part extends, and
wherein the other of the first fiber bundle and the second fiber bundle is provided so as to extend along a direction perpendicular to a direction in which each of the first grating structure part and the second grating structure part extends when the first grating and the second grating are viewed from a front.

6. The X-ray imaging apparatus as recited in claim 3, wherein the image processing unit is configured to generate first three-dimensional dark-field data by performing the scattering correction on the dark-field image at each of the plurality of relative rotation angles and reconstructing the dark-field image at each of the plurality of relative rotation angles for which the scattering correction has been performed in cases where a direction in which a rotation axis of the rotation mechanism extends and a direction in which each of the first grating structure part and the second grating structure part extends are aligned.

7. The X-ray imaging apparatus as recited in claim 6, wherein the image processing unit is configured to accept a change whether or not the scattering correction is performed, and in cases where a direction in which the rotation axis extends and the direction in which each of the first grating structure part and the second grating structure part extends are substantially orthogonal when the first grating and the second grating are viewed from the front, second three-dimensional dark-field data is generated by reconstructing the dark-field image at each of the plurality of relative rotation angles without performing the scattering correction and a three-dimensional image of the subject is obtained by combining the first three-dimensional dark-field data and the second three-dimensional dark-field data.

8. The X-ray imaging apparatus as recited in claim 1, wherein the image processing unit is configured to accept a change of the predetermined set value.

* * * * *